United States Patent [19]

Weston et al.

[11] Patent Number: 4,605,399
[45] Date of Patent: Aug. 12, 1986

[54] TRANSDERMAL INFUSION DEVICE

[75] Inventors: Robert E. Weston, Exeter, N.H.; Robert R. Hunter, III, Westboro, Mass.

[73] Assignee: Complex, Inc., Hampton, N.H.

[21] Appl. No.: 677,799

[22] Filed: Dec. 4, 1984

[51] Int. Cl.⁴ .............................................. A61M 7/00
[52] U.S. Cl. .................................... 604/305; 604/896
[58] Field of Search ................ 604/290, 305, 896–897

[56] References Cited

U.S. PATENT DOCUMENTS

| | | | |
|---|---|---|---|
| 1,224,862 | 5/1917 | Barker | 604/305 |
| 3,026,874 | 3/1962 | Stevens | 604/305 |
| 3,247,851 | 4/1966 | Seibert | 604/305 X |
| 3,367,332 | 2/1968 | Groves | 604/305 |
| 3,742,951 | 7/1973 | Zaffaroni | 604/897 |
| 3,797,485 | 3/1974 | Urquhart | 604/93 |
| 4,286,592 | 9/1981 | Chandrasekaran | 128/260 |
| 4,336,243 | 6/1982 | Sanvordeker | 424/28 |
| 4,363,319 | 12/1982 | Altshuler | 128/156 |
| 4,382,441 | 5/1983 | Svedman | 604/305 |
| 4,460,368 | 7/1984 | Allison et al. | 604/896 |

Primary Examiner—Dalton L. Truluck
Attorney, Agent, or Firm—Blodgett & Blodgett

[57] ABSTRACT

Device for introducing drugs and the like into the human body by infusion through the skin, consisting of a fluid delivery tube leading to a storage and distribution chamber means that is attached to a porous sheet which is in contact with the skin.

3 Claims, 5 Drawing Figures

TRANSDERMAL INFUSION DEVICE

BACKGROUND OF THE INVENTION

In medical practice, when it is desired to introduce drugs or the like into the human system slowly and continuously, it has been common practice to use intravenous injection. This is accomplished by use of a hollow needle having a flexible tube leading to a bottle that contains the drug in solution. It has also been possible to introduce the drug through the skin by osmosis or infusion, as in the case of nitroglycerin, in cases where the amount of drug to be introduced is small and the infusion is to take place very slowly. However, both of these methods have shortcomings. The intravenous injection into the vein is uncomfortable and sometimes dangerous. Furthermore, an I.V. injection must be performed by a "skilled" medical professional. It certainly limits the activity of the patient. In the case of children, the pain of injecting the needle is a considerable problem. On the other hand, the infusion pad used with nitroglycerin and the like allows only a limited amount of fluid to enter the skin; furthermore, the release of drug from the reservoir contained in the pad is such that the rate of infusion takes place very strongly with a new pad, but, as time passes, the rate decreases because of the amount of drug in the reservoir has been reduced. Also, the conventional infusion pad (containing a reservoir of the medication) has a limited "shelf life" and is ineffective after a certain period. These and other difficulties experienced with the prior art devices have been obviated in a novel manner by the present invention.

It is, therefore, an outstanding object of the invention to provide a transdermal infusion device giving the combined advantages of intravenous introduction and the use of an infusion pad.

Another object of this invention is the provision of a transdermal infusion device which allows continuous introduction of a drug without the rate of infusion falling during the process.

A further object of the present invention is the provision of a device for the transdermal infusion of a drug, which device is simple in construction, which is inexpensive to manufacture, and which is capable of a long use with a minimum of care.

It is another object of the instant invention to provide a device for the introduction of a drug continuously into the human body without piercing the skin, wherein the rate of introduction is maintained at a constant level.

Another object of the invention is the provision of a drug-introduction device that can be placed by a person who is not a skilled medical professional.

A further object of the invention is a pad having an unlimited shelf life, since it is stored free of medication.

With these and other objects in view, as will be apparent to those skilled in the art, the invention resides in the combination of parts set forth in the specification and covered by the claims appended hereto.

SUMMARY OF THE INVENTION

In general, the invention consists of a transdermal infusion device having an impervious main sheet and having a manifold sheet attached to one side of the main sheet to provide a storage chamber, such as a passage complex. A flexible fluid delivery tube extends through the main sheet into the passage complex of the manifold sheet. A porous sheet is attached to the manifold sheet and is adapted to lie against the human skin to release fluid thereto.

More specifically, an adhesive layer located in a peripheral area is provided on the said one side of the main sheet and completely surrounds the manifold sheet and the porous sheet. A release sheet overlies the adhesive peripheral area of the main sheet as well as the porous sheet and the manifold sheet.

BRIEF DESCRIPTION OF THE DRAWINGS

The character of the invention, however, may be best understood by reference to one of its structural forms, as illustrated by the accompanying drawings, in which.

DESCRIPTION OF THE PREFERRED EMBODIMENT

Figure 1:
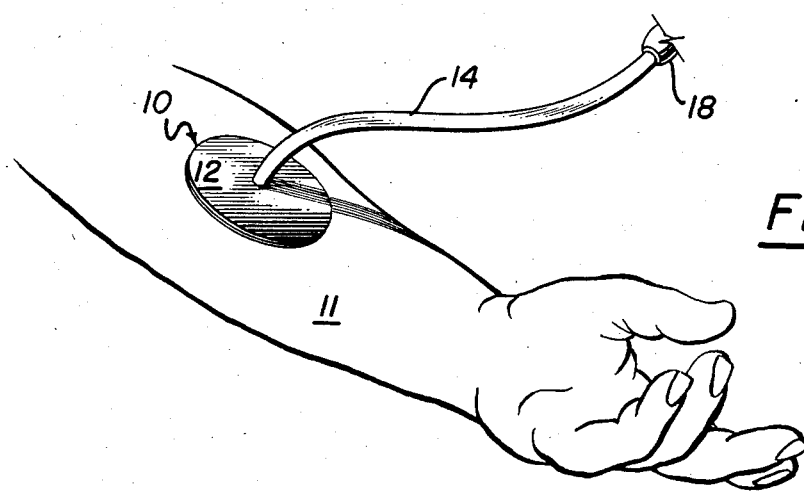
FIG. 1 is a perspective view of a transdermal infusion device incorporating the principles of the present invention and being shown in use with a portion of a human anatomy.

Referring first to FIG. 1, wherein are best shown the general features of the invention, the transdermal infusion device, indicated generally by the reference 10, is shown in use on the skin 11 of a human being. Facing away from the skin is an impervious main sheet 12 from which extends a flexible fluid delivery tube 14, preferably formed of a clear elastomer, such as polyethylene. At the outer end of the tube 14 is mounted a luer connection 18.

Figure 2:
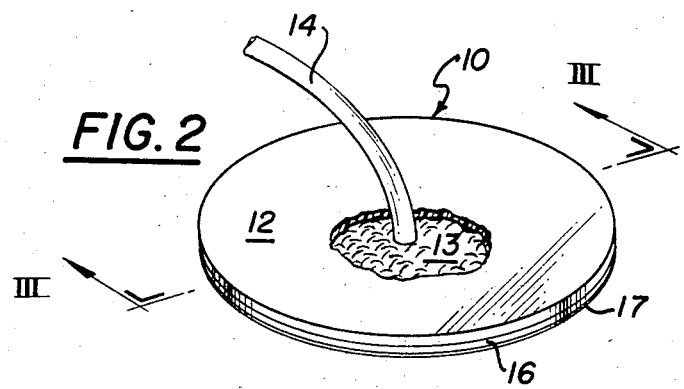
FIG. 2 is an enlarged perspective view of the infusion device.
Figure 3:
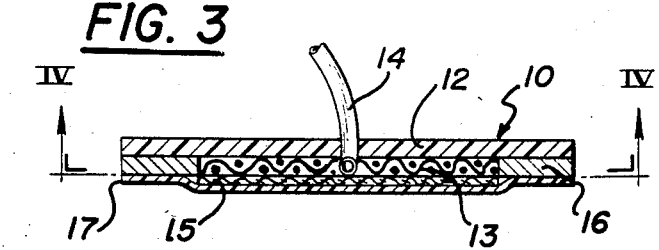
FIG. 3 is a sectional view of the infusion device taken on the line III—III of FIG. 2.

In FIGS. 2 and 3, it can be seen that a manifold sheet 13 underlies and is fastened to the side of the main sheet 12 facing toward the skin 11, the manifold sheet providing a storage chamber such as a passage complex. The tube 14 passes through the main sheet 12 and is locked in place under the manifold sheet 13. A porous sheet 15 is attached to the manifold sheet and is adapted to lie directly against the skin 11 to release fluid thereto.

Figure 4:
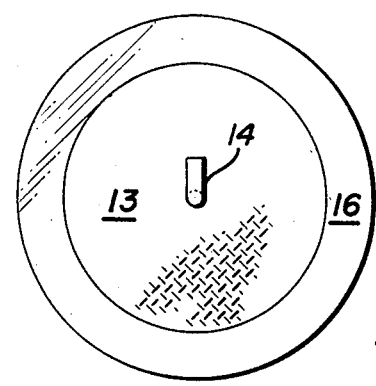
FIG. 4 is a sectional view of the device taken on the line IV—IV of FIG. 3.

As is shown in FIG. 4, the manifold sheet 13 is circular and is spaced inwardly from the periphery of the main sheet 12, thus leaving a peripheral area which in turn is covered with an adhesive layer 16 which completely surrounds the manifold sheet and the porous sheet 15. As indicated in FIGS. 2 and 3, the adhesive layer 16 and the porous sheet 15 are covered before use by a release sheet 17 that is removed before the device is used. As shown in FIGS. 3 and 4, the porous sheet 15 is coextensive with the manifold sheet 13. In the preferred embodiment, the manifold sheet 13 is a screen and the storage chamber or passage complex consists of spaces defined by woven strands which form the screen. Also, in the preferred embodiment, the main sheet is formed of a foamed polymer plastic, while the manifold sheet is in the form of a screen made of strands of a polymer plastic and the porous sheet 15 is gauze.

The operation and advantages of the present invention will now be readily understood in view of the above description. In order to use the transdermal infusion device 10, it is first necessary to peel off the release sheet 17. This exposes the adhesive 16 and allows the device to be pressed against the skin 11 in order to secure proper operation, the periphery of the main sheet 12 is pressed downwardly so that the adhesive 16 forms a seal entirely around the periphery. Fluid is then induced into the tube 14 by connecting the luer connector 18 to a conventional intravenous bottle (not shown). The fluid passes down the tube and out the lower end which is buried in the passage complex or storage chamber formed by the strands making up the manifold sheet 13. Fluid flows in all directions under the impetus of the manifold and, when properly selected, is assisted by capillary action to flow among the passages. From that point the fluid flows downwardly into the porous sheet 15 which is in the form of gauze and passes through that sheet into the skin 11 where it is absorbed in the usual way by the infusion principle. If the adhesive layer 16 is properly pressed and placed against the skin, it forms a dam from which the fluid passing through the porous layer 15 cannot escape, so that the fluid is held in place against the skin until it is absorbed. A proper selection of the tube 14 and its connection through valves to the intravenous set will produce a degree of gravitational pressure within the system and assist in feeding the fluid through the porous layer 15 into the skin.

It can be seen, then, that the pressure and concentration of fluid against the skin remains at a constant value and is widely dispersed because of the spreading action of the manifold sheet 13. It is not necessary to pierce the skin (as is true in connection with the conventional intravenous needle) nor does the osmotic pressure decrease by absorption of the fluidize drug as in the case of the conventional transdermal infusion pad. In the case of children, the advantages of this type of medication introduction is obvious. The main sheet 12 can, if desired, contain entertaining writings and pictures to make the system more pleasing to a child. At the same time, a patient can move without the danger of injuring himself or removing the needle from the vein. Furthermore, in most cases, the leakage of fluid is at a minimum.

Figure 5:
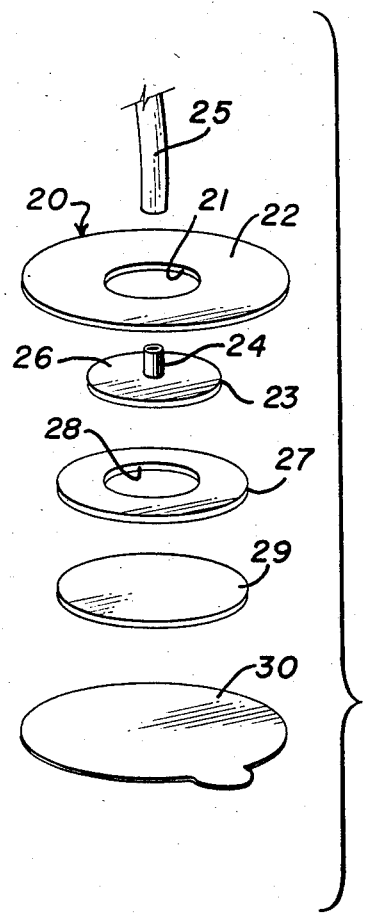
FIG. 5 is an exploded view of a modification of the invention.

FIG. 5 shows a modified form of the transdermal infusion device 20 including a main sheet 22 having a central aperture 21. An integral plastic element 23 is provided having a neck 24 extending through the aperture 21 and connected to a feed tube 25; the element 23 has a broad flange 26 which is located on the inner side of the main sheet and held there by a coating of pressure sensitive adhesive with which the entire inner surface of the main sheet is provided. A foil sheet 27 covers the flange 23 and is slightly larger than the flange, so that it engages and is sealed by the adhesive. A large aperture 28 is formed in the foil sheet concentric of the neck 24. A porous sheet 29 is attached to the foil sheet by adhesive and the entire assemblage of element 23, foil sheet 27, and porous sheet 29 are enclosed by a release sheet 30 which is held in place by the adhesive at the peripheral area of the main sheet 22 outside of the foil sheet 27.

There is no adhesive in the engaging surfaces of the device 23 and the foil 27, so that a storage chamber is formed between them to distribute the fluid medication over a broad surface of the porous sheet 29.

It is obvious that minor changes may be made in the form and construction of the invention without departing from the material spirit thereof. It is not, however, desired to confine the invention to the exact form herein shown and described, but it is desired to include all such as properly come within the scope claimed.

The invention having been thus described, what is claimed as new and desired to secure by Letters Patent is:

1. Transdermal infusion device, comprising:
   (a) an impervious main sheet formed of a foamed polymer plastic,
   (b) a manifold sheet attached to one side of the main sheet and providing a passage complex in the form of a screen made up of strands of a polymer plastic,
   (c) a flexible fluid delivery tube extending through the main sheet and into the passage complex of the manifold sheet,
   (d) a porous sheet formed of gauze attached to and coextensive with the manifold sheet and adapted to lie against a human skin to release fluid thereto,
   (e) an annular adhesive layer in a peripheral area provided on the said one side of the main sheet and completely surrounding both the manifold sheet and the porous sheet, and
   (f) a release sheet overlying the adhesive peripheral area of the main sheet, as well as the porous sheet and the manifold sheet.

2. Transdermal infusion device, comprising:
   (a) an impervious main sheet,
   (b) a manifold sheet attached to one side of the main sheet and providing a passage complex,
   (c) a flexible fluid delivery tube extending through the main sheet and into the passage complex of the manifold sheet, the outer end of the delivery tube being provided with a luer connector,
   (d) a porous sheet attached to and coextensive with the manifold sheet and adapted to lie against a human skin to release fluid thereto,
   (e) an annular adhesive layer in a peripheral area provided on the said one side of the main sheet and completely surrounding both the manifold sheet and the porous sheet, and
   (f) a release sheet overlying the adhesive peripheral area of the main sheet, as well as the porous sheet and the manifold sheet.

3. Transdermal infusion device as recited in claim 2, wherein the manifold sheet consists of a woven screen and the passage complex consists of spaces defined by the strands forming the screen.

* * * * *